US012797000B2

(12) United States Patent
Mutet et al.

(10) Patent No.: US 12,797,000 B2
(45) Date of Patent: *Nov. 17, 2026

(54) SYSTEM FOR MONITORING GASTRO-INTESTINAL DISORDERS

(71) Applicant: FONDATION DE COOPERATION SCIENTIFIQUE, Strasbourg (FR)

(72) Inventors: Bruno Mutet, Haguenau (FR); Lee Swanstrom, Portland, OR (US); Cristians Alejandro Gonzalez Cabrera, Strasbourg (FR)

(73) Assignee: FONDATION DE COOPERATION SCIENTIFIQUE, Strasbourg (FR)

( * ) Notice: Subject to any disclaimer, the term of this patent is extended or adjusted under 35 U.S.C. 154(b) by 321 days.

This patent is subject to a terminal disclaimer.

(21) Appl. No.: 18/551,246

(22) PCT Filed: Mar. 18, 2022

(86) PCT No.: PCT/EP2022/057162

§ 371 (c)(1),
(2) Date: Sep. 19, 2023

(87) PCT Pub. No.: WO2022/200212

PCT Pub. Date: Sep. 29, 2022

(65) Prior Publication Data

US 2024/0172987 A1 May 30, 2024

(30) Foreign Application Priority Data

Mar. 20, 2021 (EP) .................................... 21305347

(51) Int. Cl.

| | |
|---|---|
| ***A61B 5/00*** | (2006.01) |
| ***A61B 5/0538*** | (2021.01) |
| ***A61B 5/145*** | (2006.01) |

(52) U.S. Cl.

CPC .......... *A61B 5/4233* (2013.01); *A61B 5/0022* (2013.01); *A61B 5/0538* (2013.01); *A61B 5/14539* (2013.01); *A61B 5/7246* (2013.01)

(58) Field of Classification Search

CPC ... A61B 5/4233; A61B 5/0022; A61B 5/0538; A61B 5/14539; A61B 5/7246;

(Continued)

(56) References Cited

U.S. PATENT DOCUMENTS

2011/0307027 A1* 12/2011 Sharma .............. A61N 1/37235 607/40
2024/0172988 A1* 5/2024 Mutet .................. A61B 5/0537

OTHER PUBLICATIONS

International Search Report and Written Opinion issued on Jul. 7, 2022, in corresponding International Application No. PCT/EP2022/057162, 11 pages.

* cited by examiner

*Primary Examiner* — Jonathan T Kuo
(74) *Attorney, Agent, or Firm* — Maier & Maier, PLLC

(57) ABSTRACT

A system for monitoring Gastro-intestinal disorders including: a gastro-intestinal probe; at least one sensor configured to measure a parameter of the patient; a processor configured to: determine a first and second values corresponding to a given time interval, wherein the first value is determined based on a measurement of the parameter and the second value is determined based on a measurement of gastro-esophageal content corresponding to the given time interval; and determine a level of gastro-intestinal disorder based on the determined set of pairs of values.

20 Claims, 2 Drawing Sheets

(58) Field of Classification Search
CPC ....... A61B 5/123; A61B 5/4238; A61B 5/486; A61B 5/01; A61B 5/0816; A61B 5/1116; A61B 5/1118; A61B 5/14542; A61B 5/14546; A61B 5/021; A61B 5/024; A61B 5/4842; A61B 5/7475; A61B 2562/043; A61B 5/165
See application file for complete search history.

SYSTEM FOR MONITORING GASTRO-INTESTINAL DISORDERS

CROSS-REFERENCE TO RELATED APPLICATIONS

This application the National al Stage of International Application No. PCT/EP2022/057162, filed on Mar. 18, 2022, which claims the benefit of European Patent Application No. 21 305 347.3, filed Mar. 20, 2021, the disclosure of which is incorporated by reference herein in its entirety.

FIELD

The present subject disclosure generally relates to the domain of medical devices, and more specifically to systems for monitoring gastro-intestinal disorders.

BACKGROUND

Gastro-intestinal disorders have different forms and various levels of health consequence and impact on quality of life.

A large part of the diagnosis is done based on patient reported symptoms (PRS) and perceptions.

Diagnosis may also be based on systems relying on internal probes that are either swallowed or temporarily implanted against the gastro-intestinal tract wall of a patient to measure or capture information regarding the gastro-esophageal content. The gastro-esophageal content measurements (GECM) are sent and stored in a patient worn device. For example, the diagnosis may be based on a score determined from the GECM. This score may correspond to an overall duration during which the GECM is below a threshold.

However, these technics lack efficiency and precision. Indeed, the diagnosis relies directly on a raw measurement taking into account non-significant or non-relevant measures which can interfere with the diagnosis.

Therefore, there is a need to take into account the specificities of the patient's behaviors in the diagnosis of gastro-intestinal disorders.

SUMMARY

The present subject disclosure aims at improving the situation.

To that end, the present subject disclosure relates to a system for monitoring gastro-intestinal disorders comprising:

- A gastro-intestinal probe configured to perform gastro-esophageal content measurements of a patient;
- At least one sensor configured to measure a parameter of the patient, said parameter being dependent to a patient activity and/or a patient movement and posture;
- A processor configured to:
- determine a set of pairs of values respectively corresponding to a set of different time intervals, each pair of values corresponding to a given time interval among the set of different time intervals comprises a first value and a second value,
- wherein, said first value is determined based on a measurement of the parameter corresponding to the given time interval, and
- wherein said second value is determined based on a measurement of gastro-esophageal content corresponding to the given time interval; and
- determine a level of gastro-intestinal disorder based on the determined set of pairs of values.

It enables to enhance the accuracy of the diagnosis. Indeed, the context or behavior of the patient at the time of measurement has a strong impact on the relevance of measurement. Therefore, based on the parameter, that is, the activity and/or movement and posture of the patient, the invention enables to exclude non-significant or non-relevant measures (that is, variation of the measures of the GECM that are not disease related and therefore can interfere with the diagnosis, for example, variation due to meals and drinks or sports). Thus, based on the level of gastro-intestinal disorder an accurate diagnosis can be given.

In other words, the present subject disclosure enables to take into consideration the activity of the patient when determining the level of gastro-intestinal disorder. Indeed, evolution of the GECM may not be representative of Gastro-intestinal disorders, for example, doing sports may increase the GECM regardless of any Gastro-intestinal disorders. Therefore, the diagnosis is more accurate, for example, by not taking into account GECM related to the activity of the patient. This can be done by weighting the measurement of gastro-esophageal content according to the parameter.

Based on the coupling (also referred to as correlation) of the second value (that is, the value determined based on the GECM) with the first value, the level of gastro-intestinal disorder is therefore more relevant. This score may be obtained by weighting the events revealed by the second value which is based on measurement of gastro-esophageal content by the first value.

By gastro-intestinal probe it is understood any probe, especially internal probes that can measure through time a parameter of the gastro-esophageal content, for example, the pH of the gastro-esophageal content.

By patient activity it is understood any activity that occurs during measurement of the gastro-esophageal content. For example, the activities of the patient may relate to meals and drinks, sleeping, working, running, walking, travelling, stressful activities, state of fatigue, etc. Intensity and duration may be taken into account regarding the outputs of the sensor, for example, the evolution of the parameter through time.

By a set of different time intervals it is understood all-time division of a time period during which the gastro-esophageal content is measured. The time division can be predetermined, for example, a time partition in which each time interval is of the same duration. The time division can also be determined during the medical monitoring. For example, each gastro esophageal content measurement event, that is, each time a significant evolution of the parameter is measured starts a time interval which duration may be either the same for all the time interval, or different, for example, based on the intensity of the gastro esophageal content measurement event or until the next gastro esophageal content measurement event.

By parameter corresponding to a given time interval it is understood that the measurement of the parameter has been carried out in the given time interval.

By measurement of gastro-esophageal content corresponding to the given time interval it is understood that the measurement of gastro-esophageal content has been carried out in the given time interval.

The determination of the level of gastro-intestinal disorder can be determined as a score related to the level of gastro-intestinal disorder, said score being determined based on the determined set of pairs of values.

The first value is determined based on a measurement of the parameter, or more specifically on data representing the measurement of the parameter.

By weighting a measurement of the GECM according to the patient activity and/or a patient movement and posture, it is understood that the level of GECM measured is either valued or devalued according to the level or evolution of the parameter.

The sensor may be one among one among an accelerometer sensor, a gyroscope sensor, heart rate sensor, an output of a blood pressure sensor, an output of a temperature sensor, an output of a breathing rate sensor, an output of an oxygen saturation sensor and a flexible angular sensor In addition, the first value may be determined based on an output of a clock, a geolocation information and/or an activity input given by the patient. The measurement of the parameter may therefore be adapted according to this information.

In addition, the first value may be determined based on a past first value determined based on a past measurement of the parameter. Therefore, the determination of the first value is enhanced, reducing determination of a first value corresponding to an activity, a movement or a posture which does not correspond to the activity, the movement or the posture of the patient P.

Advantageously, the time duration between the time interval corresponding to the first value and the time interval corresponding to the past first value is below a threshold. This enables to enhance the correlation between the activity, the movement or the posture corresponding to the first value and the activity, the movement or the posture corresponding to the past first value. Therefore, the determination of the first value based on the past first value is more relevant.

Advantageously, the past measurement corresponds to a measurement with a low risk of error when determining the first value. Put in another way, only one or few activities, movements or postures are possible according to the past measurement. Therefore, the risk is low of propagating an error in the determination of the past first value to the determination of the first value.

According to an aspect of the present subject disclosure, the gastro-intestinal probe comprises at least one probe sensor among a pH sensor and a impedance sensor; and wherein said gastro-esophageal content measurements are obtained based on the output of the at least one probe sensor.

Advantageously, the GECM can be obtained by a plurality of probe sensors arranged in array. This enables to determine the direction and speed of movement of the gastro-esophageal content in the gastro-intestinal tract.

According to an aspect of the present subject disclosure, the system may further comprise a patient interface configured to receive inputs from the patient, said inputs corresponding to patient reported symptoms, PRS, wherein the level of gastro-intestinal disorder is determined based on the determined set of pairs of values and the inputs.

By taking into account the PRS inputted by the patient it enables to identify if GECM events match with PRS events enabling a more accurate diagnosis.

According to an aspect of the present subject disclosure, the system may further comprise another sensor configured to measure another parameter of the patient, said another parameter being dependent to pain and/or stress of the patient, wherein inputs corresponding to the PRS are adapted according to measures of the another parameter.

It enables to enhance the accuracy of the diagnosis. Indeed, PRS experienced by the patient are somatic and therefore highly subjective. Thus, some patients describe high pain while others do not feel any pain for the same phenomena. Therefore, by taking into consideration another parameter dependent to pain and/or stress of the patient to adapt inputs the inputs corresponding to the PRS, it enables to have an objective vu of the intensity of PRSs.

According to an aspect of the present subject disclosure, the system further comprises a receiving wireless communication unit configured to receive gastro-esophageal content measurements (more precisely data representing GECM) from the gastro-intestinal probe, and wherein the gastro-intestinal probe comprises a transmitting wireless communication unit configured to transmit gastro-esophageal content measurements.

Therefore, the data representing the GECM can be extracted from the probe to be analyzed while the probe is still in the gastro-intestinal tract.

In addition, the wireless communication unit can be included in a device, for example, a user equipment (smart phone, connected watch) or a patient worn device. Therefore, the patient can live normally which enables to monitor the patient during its day-to-day life, which is more relevant to establish an accurate diagnosis.

According to another aspect of the present subject disclosure, the system comprises the gastro-intestinal probe, a patient worn device comprising at least one sensor configured to measure the parameter of the patient and a user equipment. The probe, the patient worn device and the user equipment have wireless communication capacity.

The user equipment's interface (for example the interface of a smartphone) can be used to collect data related to PRS while the sensor can be one among the sensors already present on the smartphone.

According to another aspect of the present subject disclosure, the system associates the level of gastro-intestinal disorder to a specific gastro-intestinal disorder by correlating events revealed by the first value and the second value.

This enables to determine a specific disease among gastro-intestinal diseases. Indeed, each gastro-intestinal disease has a specific GECM depending on the activity of the patient (some specific gastro-intestinal disorder only occur when the patient practices certain activity).

In addition, the system may determine another level of gastro-intestinal disorder related to another gastro-intestinal disorder by correlating events revealed by the first value and the second value. The determination of the another level is performed by the system in the same manner (even though the correlation may be different, for example, by weighting differently the events revealed by the second value with the first value) as to determine the level of gastro-intestinal disorder related to the gastro-intestinal disorder.

The another sensor may be one among a heart rate sensor, a blood pressure sensor, a temperature sensor, a breathing rate sensor, an oxygen saturation sensor, a lactate level sensor, a sodium level sensor, a uric acid level sensor, a potassium level sensor, a stress-related hormones sensor.

A second aspect of the present subject disclosure concerns a method to monitor Gastro-intestinal disorders comprising:

- receiving data representing gastro-esophageal content measurements of a patient;
- receiving data representing parameter measurements, said parameter being dependent to a patient activity and/or a patient movement and posture;
- determining a set of pairs of values respectively corresponding to a set of different time intervals, each pair of values corresponding to a given time interval among the set of different time intervals comprises a first value and a second value, wherein said first value is determined based on a data representing a measurement of the parameter corresponding to the given time interval, and wherein said second value is determined based on data representing a measurement of gastro-esophageal content corresponding to the given time interval; and determining a level of gastro-intestinal disorder based on the determined set of pairs of values.

A third aspect of the present subject disclosure concerns a computer program product comprising code instructions to perform the method as described previously when said instructions are run by a processor.

A fourth aspect of the present subject disclosure concerns a computer comprising:

A communication interface configured to:

receive data representing gastro-esophageal content measurements of a patient;

receive data representing parameter measurements, said parameter being dependent to a patient activity and/or a patient movement and posture;

the computer further comprising a processor configured to:

determine a set of pairs of values respectively corresponding to a set of different time intervals, each pair of values corresponding to a given time interval among the set of different time intervals comprises a first value and a second value, wherein said first value is determined based on a data representing a measurement of the parameter corresponding to the given time interval, and wherein said second value is determined based on data representing a measurement of gastro-esophageal content corresponding to the given time interval; and determine a level of gastro-intestinal disorder based on the determined set of pairs of values.

BRIEF DESCRIPTION OF DRAWINGS

The present subject disclosure is illustrated by way of example, and not by way of limitations, in the figures of the accompanying drawings, in which like reference numerals refer to similar elements and in which.

DETAILED DESCRIPTION

Figure 1:
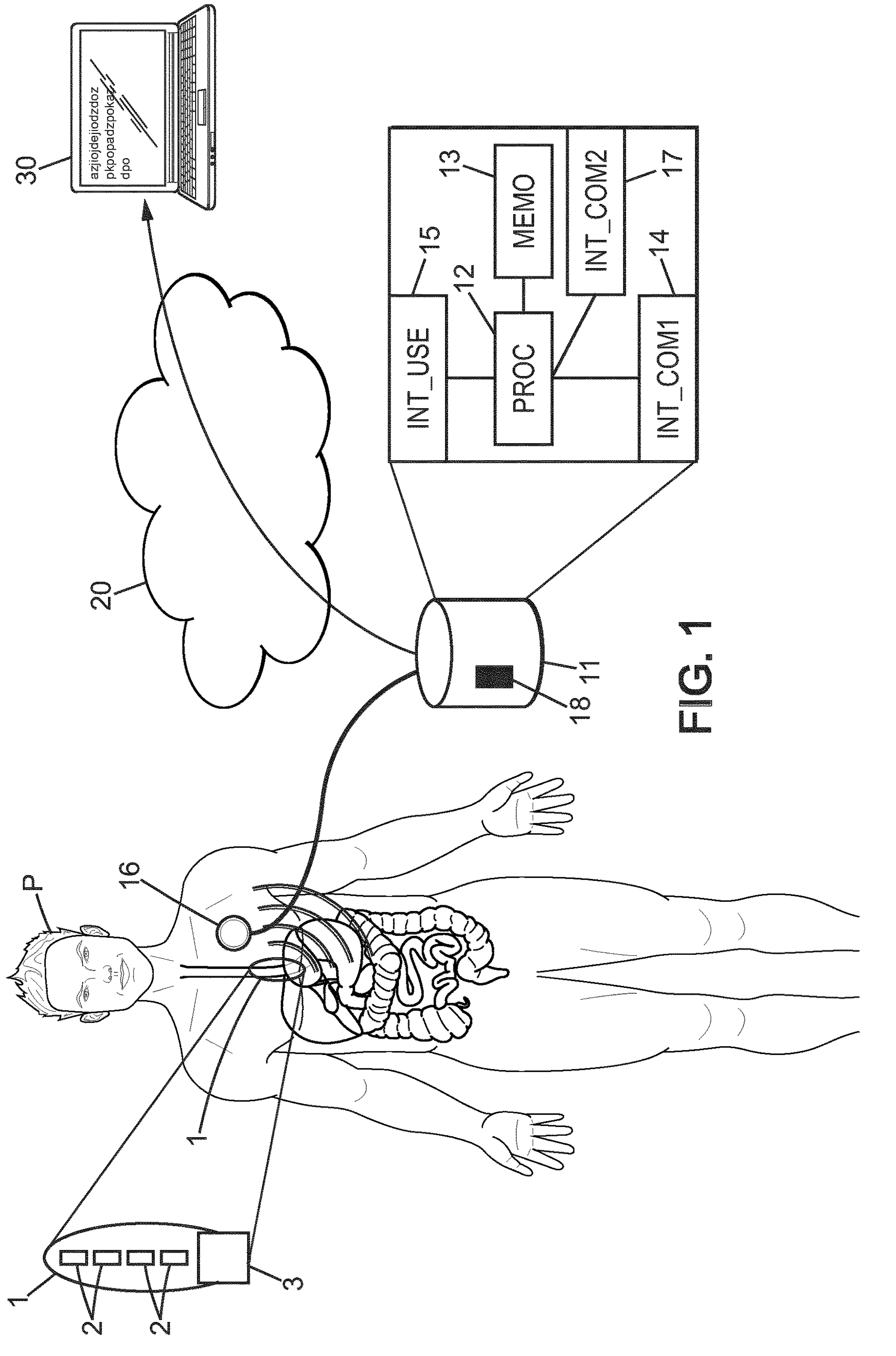
FIG. 1 illustrates a system according to an embodiment of the present subject disclosure.

Referring to FIG. 1, there is shown a patient P with a gastro-intestinal probe 1 in its gastro-intestinal tract and a wearable device 11. The gastro-intestinal probe 1 comprises a plurality of probe sensors 2 arranged in array. The probe sensors 2 may be pH sensors and/or impedance sensors, these sensors output gastro-esophageal content measurements. The gastro-intestinal probe 1 comprises a wireless communication unit 3 which is configured to transmit the gastro-esophageal content measurements obtained via the probe sensors 2 to the wearable device 11.

The wearable device 11 (which could also be a user equipment) comprises a sensor 16 configured to measure a parameter of the patient, for example, the heartbeat of the patient P. More generally, the sensor 16 is of any type of sensor enabling to measure a parameter dependent to the patient P activity and/or the patient P movement and posture. Several sensors can be combined to track the patient P activity and/or the patient P movement and posture. The sensor 16 may be a sensor among an accelerometer sensor, a gyroscope sensor, heart rate sensor, an output of a blood pressure sensor, an output of a temperature sensor, an output of a breathing rate sensor, an output of an oxygen saturation sensor and a flexible angular sensor.

The wearable device 11 comprises a pain and stress sensor 18. The pain and stress sensor 18 may be one among a heart rate sensor, a blood pressure sensor, a temperature sensor, a breathing rate sensor, an oxygen saturation sensor, a lactate level sensor, a sodium level sensor, a uric acid level sensor and a potassium level sensor.

The wearable device 11 comprises a patient interface 15 configured to receive inputs from the patient P corresponding to PRS and/or an activity input. The activity input refers to information inputted by the patient P and indicating an activity, for example, having lunch or doing sports. The wearable device 11 also comprises a wireless communication module 14, one processing module 12, a memory unit 13 and a communication module 17. The memory unit 13 comprises a non-volatile unit which retrieves the computer program and a volatile unit which retrieves the parameters used for establishing a score representative of a level of gastro-intestinal disorder, like a predefined length of the time intervals.

The wireless communication module 14 is configured to receive the gastro-esophageal content measurements transmitted by the wireless communication unit 3.

The wireless communication unit 3 and the wireless communication module 14 can use any wireless communication technologies and standard enabling to perform a wireless communication at a distance of about 1 meter, for example, LPWANs (Lora, Sigfox), cellular (3G, 4G, 5G), Mesh protocols (Zigbee), Bluetooth and BLE, Wifi or RFID.

The communication module 17 is configured to transmit data via a network 20 (for example, via internet using IP technology) to a computer 30, this computer being for example, the computer of the doctor which conducts the monitoring of the patient P to diagnosis a possible gastro-intestinal disorder.

The processing module 12 is configured to determine a set of time intervals, and for each time interval, to determine a first value and a second value. The processing module 12 is also configured to determine a score representative of a level of gastro-intestinal disorder. The processing module 12 is configured to determine the first value based on the output of the sensor 16 and/or on an activity input.

Thus, in the example of FIG. 1, the processor module 12 does all the computing required to determine the score representative of a level of gastro-intestinal disorder, however, the present subject disclosure is not limited to such embodiment. Therefore, any or all of the computing required to determine the score can be done on the computer 30 of the doctor or on any other computer and/or server. For example, the communication module 17 can be configured to transmit the measurements received from the gastro-intestinal probe 1, the outputs of the sensor 16 and the pain and stress sensor 18 and the inputs in the patient interface 15 to the computer 30 of the doctor. Based on these received data, the computer 30 of the doctor can compute the first and second value and finally the score representative of a level of gastro-intestinal disorder.

Figure 2:
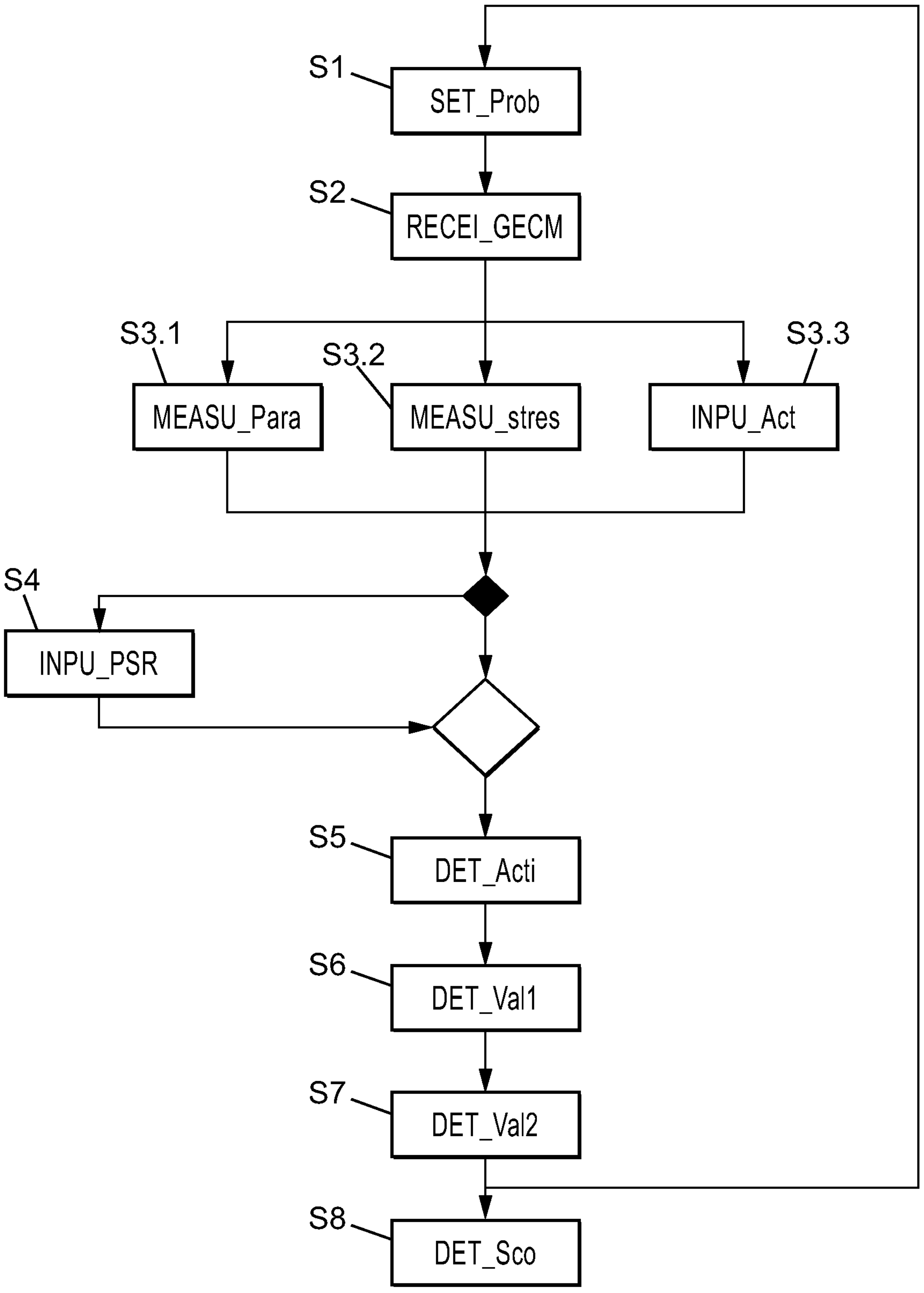
FIG. 2 illustrates a flowchart representing the implementation of a system according to the present subject disclosure.

Referring to FIG. 2, illustrates a flowchart representing the implementation of a system according to the present subject disclosure.

At step S1 the gastro-intestinal probe 1 is set in the gastro-intestinal tract of the patient P to be monitored for Gastro-intestinal disorders.

At step S2 the wearable device 11 receives GECMs from the probe 1.

When a specific GECM event occurs, the processing module 12 determines a time interval which begins at the time the GECM event is measured. The time interval lasts for a predetermined time T. As previously mentioned the time interval may be defined differently. For example, the duration of the time interval may depend on the intensity or the level of the GECM.

The GECM event is a significant variation and/or a significant level of GECM and/or a duration of GECMs above à level. For example, if the pH measured by the probe sensors 2 is under a certain level or if the pH measured decrease of a certain amount, then a GECM event is identified by the processing module 12.

At step S3.1, during the time interval, the wearable device 11 measures the level and tracks the evolution of the parameter through the sensor 16.

At step S3.2, during the time interval, the wearable device 11 receives signals from the pain and stress sensor 18.

At step S3.3, during the time interval, the wearable device 11 receives an activity input from the patient P through the patient interface 15.

The steps S3.2 and S3.3 are optional.

At step S4, during the time interval, the wearable device 11 receives a PRS from the patient P through the patient interface 15. The PRS may combine a type of symptom (for example, heartburn, chest pain, pyrosis, belching, dysphagia, regurgitation or cough and a level of intensity of this symptom. Step S4 is optional.

At step 5, the processing module 12 determines an activity performed by the patient P during the time interval based on the activity input and/or on the signals received from the sensor 16. For example, if the sensor 16 is a temperature sensor and if the signal received from this temperature sensor corresponds to a low body temperature and that no activity input has been inputted, the activity of the patient may be considered as sleeping. For example, if the sensor 16 is a heart rate sensor and if the signal received from this heart rate sensor corresponds to a high heartbeat, the patient may be considered as doing sports. Alternatively or in complementary, sensor 16 may also be configured to measure a parameter dependent on a movement and posture of the patient P. For example, the output of such sensor 16 may indicate that during the time interval the patient P is lying down, bending over, running, walking, doing sports or sleeping. This activity is determined according to the activity input when such input is performed by the patient P.

The processing module 12 may also determine the intensity of the activity and or its duration. Therefore, an activity started long before will not have the same effect on the GECM than an activity that has just started.

At step 6, the processing module 12 determines the first value. The first value may be a score expressing the impact of the activity on the GECM measured. Therefore, the first value may depend on one or several among the activity, the movement, the posture, the intensity of the activity and/or the duration of the activity. For example, the first value will be high when the patient is running for one hour before the time interval corresponding to the first value, while the first value will be low when the patient starts running during the time interval corresponding to the first value. For example, the first value will be high when the patient is sleeping for four hours before the time interval corresponding to the first value, while the first value will be low when the patient starts to sleep during the time interval corresponding to the first value.

The first value may be different according to each gastro-intestinal disorder. Therefore, several first values may be determined by the processing module 12 for each time interval and each type of gastro-intestinal disorder.

At step 7, the processing module 12 determines the second value based on the measurement of gastro-esophageal content measured at step S2. For example, to the GECM that has been detected as a GECM event.

Several values of the GECM may be measured at step S2, that is, several measurements could have been performed during the time interval. This is especially the case with system performing high frequency measurement of the gastro esophageal content. In those cases the GECM used to compute the second value may be any combination of the GECM measured during the time interval, for example, the maximum GECM measured during the time interval, the average of the GECM measured during the time interval and the GECM that has been identified as the GECM event.

The steps S1 to S7 are iteratively performed to obtain a sequence of pairs of first and second value, each pair of values corresponding to its own time interval. Each iteration may involve a new time interval even though these time intervals may intersect.

At step S8, the processing module 12 determines a level of gastro-intestinal disorder. For example, by determining a score related to the level of gastro-intestinal disorder.

For example, for each pair of first and second values a third value is obtained, this third value being determined by multiplying the second value with a weighed coefficient. The weighed coefficient may be for example the first value (for example, normalized between 0 and 1). The sequence of third values obtained respectively with the sequence of pairs of first and second value is then compared to sequences of patient for which Gastro-intestinal disorders have been previously analyzed and for which diagnosis have been confirmed. The more the sequence of third values is similar to a sequence corresponding to a specific gastro-intestinal disorder and the more the score related to the level of gastro-intestinal disorder will be high.

This step can be implemented for each type of gastro-intestinal disorder provided that first values where computed for each of these types.

When step S4 is performed, the level of gastro-intestinal disorder is determined based on the determined set of pairs of values and the inputs corresponding to the PRS. For example, by weighting the first value, the second value or the third value corresponding to the time interval according to the intensity of the PSR inputted during the same time interval. In addition, when step S3.2 is performed, the intensity of the PSR can also be adapted according to measures of the another parameter, that is, according to the output of the pain and stress sensor 18. For example, a value corresponding to the input from the patient P can be weighted according to the output of the pain and stress sensor 18. Therefore, a PSR inputted while the level of the parameter dependent to pain and/or stress is low will be devalued and therefore less considered. In contrary, a PSR inputted while the level of the parameter related to pain and/or stress is high will be valued and therefore more considered.

The invention claimed is:

1. A system for monitoring gastro-intestinal disorders, comprising:

a gastro-intestinal probe configured to perform gastro-esophageal content measurements of a patient;

at least one sensor configured to measure a parameter of the patient, said parameter being dependent to a patient activity and/or a patient movement and posture; and a processor configured to:

determine a set of pairs of values respectively corresponding to a set of different time intervals, wherein each pair of values corresponding to a given time interval of the set of different time intervals comprises a first value and a second value, wherein said first value is determined based on a measurement of the parameter corresponding to the given time interval, wherein said second value is determined based on a measurement of gastro-esophageal content corresponding to the given time interval, wherein each time interval is initiated based on detection of a gastro-esophageal content measurement event, and wherein the first value represents a score expressing an impact of one or more of the patient activity and patient movement and posture on the gastro-esophageal content measurement during the given time interval; and determine a level of gastro-intestinal disorder based on the determined set of pairs of values.

2. The system according to claim 1, further comprising a patient interface configured to receive inputs from the patient, said inputs corresponding to patient reported symptoms, PRS, wherein the level of gastro-intestinal disorder is determined based on the determined set of pairs of values and the inputs corresponding to the PRS.

3. The system according to claim 2, further comprising another sensor configured to measure another parameter of the patient, said another parameter being dependent to pain and/or stress of the patient, wherein inputs corresponding to the PRS are adapted according to measures of the other parameter.

4. The system according to claim 3, wherein the other sensor is a sensor among a heart rate sensor, a blood pressure sensor, a temperature sensor, a breathing rate sensor, an oxygen saturation sensor, a lactate level sensor, a sodium level sensor, a uric acid level sensor, a potassium level sensor, a stress-related hormones sensor; and wherein measures of the other parameter are obtained based on the output of the other sensor.

5. The system according to claim 1, wherein the level of gastro-intestinal disorder is determined by weighting the second value according to the first value.

6. The system according to claim 1, wherein the sensor is one among an accelerometer sensor, a gyroscope sensor, heart rate sensor, an output of a blood pressure sensor, an output of a temperature sensor, an output of a breathing rate sensor, an output of an oxygen saturation sensor and a flexible angular sensor.

7. The system according to claim 1, wherein the first value is determined based on an output of a clock, a geolocation information and/or an activity input given by the patient.

8. The system according to claim 1, wherein the first value is determined based on a past first value determined based on a past measurement of the parameter.

9. The system according to claim 1, wherein the gastro-intestinal probe comprises at least one probe sensor among a pH sensor and a impedance sensor; and wherein said gastro-esophageal content measurements are obtained based on the output of the at least one probe sensor.

10. The system according to claim 9, wherein the gastro-intestinal probe comprises a plurality of probe sensors arranged in array, wherein said gastro-esophageal content measurements are obtained based on the outputs of the plurality of probe sensors.

11. The system according to claim 1, further comprising a receiving wireless communication unit configured to receive gastro-esophageal content measurements from the gastro-intestinal probe, and wherein the gastro-intestinal probe comprises a transmitting wireless communication unit configured to transmit gastro-esophageal content measurements.

12. The system according to claim 11, further comprising a device, said device comprising the receiving wireless communication unit and said device being a user equipment or a patient worn device.

13. A method to monitor gastro-intestinal disorders, comprising:

receiving data representing gastro-esophageal content measurements of a patient;

receiving data representing parameter measurements, said parameter being dependent to a patient activity and/or a patient movement and posture;

determining a set of pairs of values respectively corresponding to a set of different time intervals, wherein each pair of values corresponding to a given time interval of the set of different time intervals comprises a first value and a second value, wherein said first value is determined based on a data representing a measurement of the parameter corresponding to the given time interval, and wherein said second value is determined based on data representing a measurement of gastro-esophageal content corresponding to the given time interval, wherein each time interval is initiated based on detection of a gastro-esophageal content measurement event, and wherein the first value represents a score expressing an impact of one or more of the patient activity and patient movement and posture on the gastro-esophageal content measurement during the given time interval; and determining a level of gastro-intestinal disorder based on the determined set of pairs of values.

14. A non-transitory computer-readable medium encoded with executable instructions which, when executed, causes an apparatus comprising a processor operatively coupled with a memory, monitor gastro-intestinal disorders, comprising:

receiving data representing gastro-esophageal content measurements of a patient;

receiving data representing parameter measurements, said parameter being dependent to a patient activity and/or a patient movement and posture;

determining a set of pairs of values respectively corresponding to a set of different time intervals, wherein each pair of values corresponding to a given time interval of the set of different time intervals comprises a first value and a second value, wherein said first value is determined based on a data representing a measurement of the parameter corresponding to the given time interval, and wherein said second value is determined based on data representing a measurement of gastro-esophageal content corresponding to the given time interval, wherein each time interval is initiated based on detection of a gastro-esophageal content measurement event, and wherein the first value represents a score expressing an impact of one or more of the patient activity and patient movement and posture on the gastro-esophageal content measurement during the given time interval; and determining a level of gastro-intestinal disorder based on the determined set of pairs of values.

15. The non-transitory computer-readable medium according to claim 14, wherein the level of gastro-intestinal disorder is determined by weighting the second value according to the first value.

16. The non-transitory computer-readable medium according to claim 14, wherein the first value is determined based on a past first value determined based on a past measurement of the parameter.

17. The non-transitory computer-readable medium according to claim 14, wherein the first value is determined based on an output of a clock, a geolocation information and/or an activity input given by the patient.

18. A computer apparatus, comprising:

a communication interface configured to:

receive data representing gastro-esophageal content measurements of a patient;

receive data representing parameter measurements, said parameter being dependent to a patient activity and/or a patient movement and posture;

the computer apparatus further comprising a processor configured to:

determine a set of pairs of values respectively corresponding to a set of different time intervals, wherein each pair of values corresponding to a given time interval of the set of different time intervals comprises a first value and a second value, wherein said first value is determined based on a data representing a measurement of the parameter corresponding to the given time interval, and wherein said second value is determined based on data representing a measurement of gastro-esophageal content corresponding to the given time interval, wherein each time interval is initiated based on detection of a gastro-esophageal content measurement event, and wherein the first value represents a score expressing an impact of one or more of the patient activity and patient movement and posture on the gastro-esophageal content measurement during the given time interval; and determine a level of gastro-intestinal disorder based on the determined set of pairs of values.

19. The computer apparatus according to claim 18, wherein the level of gastro-intestinal disorder is determined by weighting the second value according to the first value.

20. The computer apparatus according to claim 18, wherein the first value is determined based on an output of a clock, a geolocation information and/or an activity input given by the patient.

* * * * *